(12) United States Patent
Evans et al.

(10) Patent No.: US 11,885,795 B2
(45) Date of Patent: *Jan. 30, 2024

(54) METHOD FOR MEASURING BREATH ALCOHOL CONCENTRATION AND APPARATUS THEREFOR

(71) Applicant: Alco Systems Sweden AB, Jarfalla (SE)

(72) Inventors: Nigel Evans, Vale of Glamorgan (GB); Leigh Wallington, Vale of Glamorgan (GB)

(73) Assignee: ALCO SYSTEM SWEDEN AB

( * ) Notice: Subject to any disclaimer, the term of this patent is extended or adjusted under 35 U.S.C. 154(b) by 163 days.

This patent is subject to a terminal disclaimer.

(21) Appl. No.: 17/192,147

(22) Filed: Mar. 4, 2021

(65) Prior Publication Data

US 2021/0270804 A1 Sep. 2, 2021

Related U.S. Application Data

(63) Continuation of application No. 13/995,377, filed as application No. PCT/SE2010/051421 on Dec. 20, 2010, now Pat. No. 10,942,168.

(51) Int. Cl.
*G01N 33/497* (2006.01)
*G01N 33/98* (2006.01)
(Continued)

(52) U.S. Cl.
CPC ......... *G01N 33/4972* (2013.01); *A61B 5/087* (2013.01); *A61B 5/097* (2013.01);
(Continued)

(58) Field of Classification Search
None
See application file for complete search history.

(56) References Cited

U.S. PATENT DOCUMENTS

| 4,459,994 A | 7/1984 | Slemeyer |
| 4,770,026 A | 9/1988 | Wolf |

(Continued)

FOREIGN PATENT DOCUMENTS

| CA | 2552130 A1 | 1/2007 |
| DE | 102006018970 B3 | 5/2007 |

(Continued)

*Primary Examiner* — Jacqueline Cheng
*Assistant Examiner* — Jairo H Portillo

(57) ABSTRACT

The present invention relates to a method and apparatus for measuring breath alcohol concentration of a user. A flow of an expired breath sample is passed through a fuel cell sensor giving an output signal proportional to the amount of alcohol present in the breath sample. By measuring the flow rate, the volume of the breath sample may be calculated, whereas the breath alcohol concentration is calculated based on the fuel cell output signal. Both the sample volume and the breath alcohol concentration values are continually updated by integrating the measured instantaneous flow rate and the fuel cell output signal over time. If the user stops blowing, flow compensation is performed to obtain a compensated fuel cell output signal using a stored calibration volume. Hence, an improved method for accurately measuring the breath alcohol concentration of a test person is achieved, capable of handling varied expired volumes of breath, which obviates the need for a sampling mechanism.

18 Claims, 2 Drawing Sheets

(51) Int. Cl.
    *A61B 5/087*    (2006.01)
    *A61B 5/097*    (2006.01)
    *A61B 5/00*     (2006.01)
    *B60K 28/06*    (2006.01)

(52) U.S. Cl.
    CPC ............ *A61B 5/7225* (2013.01); *A61B 5/742* (2013.01); *B60K 28/063* (2013.01); *G01N 33/98* (2013.01)

(56) References Cited

U.S. PATENT DOCUMENTS

| | | |
|---|---|---|
| 4,902,628 A | 2/1990 | Blair |
| 5,443,794 A | 8/1995 | Williams |
| 5,612,896 A | 3/1997 | Stock |
| 6,167,746 B1 | 1/2001 | Gammenthaler |
| 7,422,723 B1 | 9/2008 | Betsill |
| 7,749,169 B2 | 7/2010 | Bayer et al. |
| 2003/0176803 A1 | 9/2003 | Gollar |
| 2003/0183437 A1 | 10/2003 | Mendoza |
| 2004/0254491 A1 | 12/2004 | Ricciardelli |
| 2005/0177056 A1 | 8/2005 | Giron et al. |
| 2005/0241871 A1 | 11/2005 | Stewart et al. |
| 2005/0251060 A1 | 11/2005 | Gollar |
| 2007/0154765 A1 | 7/2007 | Bayer et al. |
| 2008/0097234 A1 | 4/2008 | Nicolazzi et al. |
| 2009/0007634 A1 | 1/2009 | Mitchell |
| 2010/0286548 A1 | 11/2010 | Lazar et al. |
| 2012/0010519 A1 | 1/2012 | Rapoport et al. |

FOREIGN PATENT DOCUMENTS

| | | |
|---|---|---|
| EP | 1326075 A1 | 7/2003 |
| FR | 2506022 A1 | 11/1982 |
| JP | 2004522944 A | 7/2004 |

METHOD FOR MEASURING BREATH ALCOHOL CONCENTRATION AND APPARATUS THEREFOR

CROSS REFERENCE TO RELATED APPLICATIONS

This application is a continuation of U.S. application Ser. No. 13/995,377 filed Jun. 18, 2013, which is a National Stage Application filed under 35 U.S.C. 371 of International Application No. PCT/SE2010/051421, filed Dec. 20, 2010, the contents of which are hereby incorporated by reference in their entireties.

FIELD OF THE INVENTION

The present invention relates to a method for measuring breath alcohol concentration of a user, as defined by the preamble of claim 1. The method comprises receiving a flow of an expired breath sample from a user and measuring the flow rate using a pressure sensor. At the same time, the breath sample is led into a fuel cell sensor. The output signal of the fuel cell sensor is used to determine the volume of alcohol present in the breath sample, and thus the breath alcohol concentration.

In a further aspect, the invention also relates to an apparatus for measuring breath alcohol concentration of a user, as defined by the preamble of claim 7. The apparatus comprises sampling means for receiving an expired breath sample of a user, means for measuring the flow rate of the sample, a fuel cell sensor and a microcontroller. The microcontroller is adapted to calculate the volume of alcohol present in the breath sample, and thus the breath alcohol concentration, based on an output signal of the fuel cell sensor

BACKGROUND OF THE INVENTION

Generally, there are two techniques employed for measuring the breath alcohol concentration and thereby determine a person's blood alcohol concentration. In a first method, infrared spectroscopy is used, whereby a breath sample from a person is subjected to infrared radiation. The molecules in the breath sample absorb specific frequencies, called resonant frequencies, which are characteristic to the molecules. For example the absorption by ethanol molecules gives rise to a specific infrared spectrum which may be used to determine the amount of ethanol present in the breath sample, and thus the breath alcohol concentration. Although this method gives high measuring accuracy, sensors incorporating infrared spectroscopy are expensive, which limits application in mass-produced devices.

A second commonly used technology is based on a fuel cell sensor which converts fuel in the shape of alcohol (ethanol) to electric current in an electrochemical reaction. Fuel cell sensors have a somewhat lower accuracy than infrared spectroscopy sensors, but are much cheaper. However, fuel cell sensors require that the breath sample is of a determinable volume in order to correctly determine the breath alcohol concentration.

Traditional fuel cell based analyser systems operate by means of a mechanical sampling system which draws a pre-specified volume of breath into the fuel cell for analysis. The mechanical means may comprise motors, solenoid valves, piston-cylinder devices, diaphragm mechanisms or push buttons connected to a pump or bellows system. In U.S. Pat. No. 6,167,746 there is disclosed an apparatus comprising an electronically controlled valve to ascertain that a requisite volume of breath is passed through a fuel cell. US 2005/0241871 discloses a sobriety interlock device comprising a pressure transducer and a solenoid valve operating independently of each other providing a variable flow of breath to a fuel cell. A microprocessor instructs the solenoid valve to remain open for a finite period of time to give a predetermined breath sample volume, and calculates an algorithmic correction factor based on pressure readings to provide a pressure compensated alcohol result.

The methods described in the prior art involve advanced control circuitry and complex or bulky mechanical components which introduce extra cost to the system and limit the ability to reduce the size of the system without compromising accuracy.

Hence, there is a need for improved methods for measuring breath alcohol concentration with high accuracy, which allow for compact devices that may be produced at low cost.

SUMMARY OF THE INVENTION

It is an object of the present invention to provide an improved method for measuring breath alcohol concentration with high accuracy, which allows for compact measuring devices that may be produced at low cost.

According to the present invention, there is provided a method for determining breath alcohol concentration. The method includes the following specific measures, as defined by the characterising portion of independent claim 1. From the measured flow rate, the volume of the breath sample is calculated. Throughout the expiration of the breath sample, the breath sample volume and the volume of alcohol present in the breath sample are continually updated by integrating the measured instantaneous flow rate and the fuel cell output signal over time. If the user stops blowing, flow compensation is performed wherein the fuel cell output signal is compensated using a stored calibration volume to obtain a final compensated fuel cell output signal.

By compensating the fuel cell output signal, the measuring accuracy of the method and apparatus is ensured, irrespective of the volume of the breath sample. Since the method does not require a predetermined breath sample volume, the mechanical sampling systems as used in the prior art become unnecessary, and the measuring apparatus may be made more compact with fewer or no moving parts. Thereby the size and cost of apparatus may be greatly reduced.

In preferred embodiments, the method according to the present invention further comprises determining the blood alcohol concentration based on the breath alcohol concentration, and displaying the resulting blood alcohol concentration.

In a preferred embodiment, the method according to the present invention comprises performing the compensation using the formula:

$$FC_{comp} = FC_{out} * \frac{V_{cal}}{V_b}$$

In a further preferred embodiment, the method according to the present invention comprises preventing start-up of a vehicle if the calculated breath alcohol concentration exceeds a predetermined threshold value.

In a further preferred embodiment, the method according to the present invention comprises, measuring the flow rate by means of a pressure-based flow meter, preferably a Venturi meter or orifice plate in combination with a pressure sensor. The pressure-based flow meter has the advantage of providing a compact component with few or no moving parts, ensuring efficient use of space in a device carrying out the method of the invention.

According to the present invention, as defined by independent claim 7, there is also provided an apparatus for determining breath alcohol concentration. The apparatus includes the following specific features, as defined by the characterising portion of independent claim 1. Based on the flow rate measurements, the microcontroller is adapted to calculate the volume of the breath sample. The microcontroller is further adapted to continually update the breath sample volume and the breath alcohol concentration by integrating the measured instantaneous flow rate and the fuel cell output signal over time. The microcontroller is configured to perform flow compensation on the fuel cell output signal to obtain a final compensated fuel cell output signal, if the user stops blowing.

Preferred embodiments of the apparatus according to the present invention comprise features corresponding to the method described above.

In a preferred embodiment, a breath alcohol interlock device comprising an apparatus for determining breath alcohol concentration according to the present invention and a vehicle comprising such an interlock device are provided.

DETAILED DESCRIPTION OF THE INVENTION

The invention will be further explained below through the detailed description of examples thereof and with reference to the accompanying drawings. It is to be understood that the invention should not be limited to the embodiments shown in the figures and described below, but may be varied to encompass any combination of equivalent features within the scope defined by the attached claims.

Figure 1:
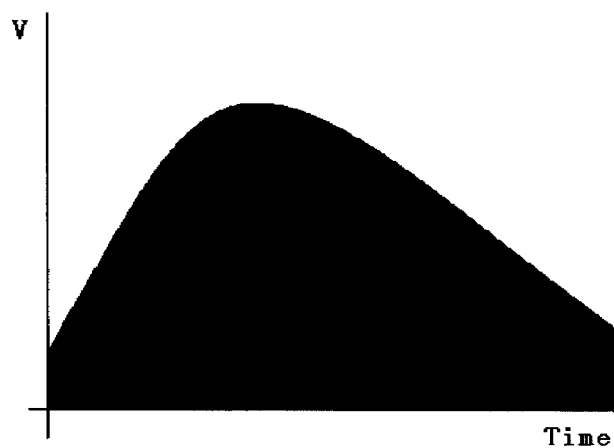
FIG. 1 is a graphical representation of a fuel cell output signal over time.

When an expired breath sample is passed through the fuel cell of a breath alcohol measuring device, also known under the name Breathalyser® (trade mark owned by Drager), any alcohol (ethanol) present in the breath sample is oxidised in an electrochemical reaction, which generates a measurable electrical current. FIG. 1 shows a typical output response from a fuel cell in a graph of the output voltage versus time. The area under the curve is calculated by integrating the voltage over time, which gives a value FC that is directly proportional to the alcohol concentration in the breath.

In order to give an accurate measurement of the breath alcohol concentration (BrAC), the breathalyser must be calibrated using a sample of known alcohol concentration and volume. When subsequently performing an alcohol breath test on a test person, the breathalyser requires a predetermined sample volume, corresponding to the one used for calibration. When the required volume is supplied, the breathalyser will compare the area under the curve of the fuel cell output signal (voltage) of the test sample with the value stored from the calibration routine and give a reading for the tested breath alcohol concentration.

The requirement of a specific sample volume represents a major inconvenience in breathalysers known in the art. Firstly, if for example the test person has reduced lung capacity, or for some other reason is not able to provide the pre-determined volume of breath sample, a valid breath test may not be performed. Secondly, the sampling mechanism needed in a breathalyser to measure and obtain a certain chosen sample volume and to furnish it to the fuel cell (e.g. pressure sensors, valves, pumps, etc.) can be rather expensive and/or bulky, which puts a constraint on the possibilities to minimise the size of the apparatus and to reduce production costs.

In a similar method as when measuring the fuel cell area, the volume of the breath sample can be determined by calculating the area under a curve of the volumetric flow rate of the sample versus time. The flow rate is measured using a suitable flow meter, e.g. mechanical, pressure-based, optical, thermal or electromagnetic. In a preferred embodiment of the present invention, a pressure-based flow meter is used such as a Venturi meter, orifice plate or equivalent in combination with a pressure sensor.

Laboratory test have proven that the variation of breath volume $V_b$ correlates linearly with the fuel cell output signal $FC_{out}$ for any specified alcohol concentration:

$$FC_{out}=k*V_b$$

By using a measured and stored calibration volume $V_{cal}$ to perform a "flow" compensation of the fuel cell output signal $FC_{out}$ and substituting the expression for the constant $k=FC_{out}/V_b$ into the corresponding equation, a compensated value for the fuel cell output signal $FC_{comp}$ is obtained:

$$FC_{comp} = FC_{out} * \frac{V_{cal}}{V_b}$$

Hence, a new and inventive method of accurately measuring the breath alcohol concentration of a test person is achieved, capable of handling varied expired volumes of breath, which obviates the need for a sampling mechanism.

Figure 2:
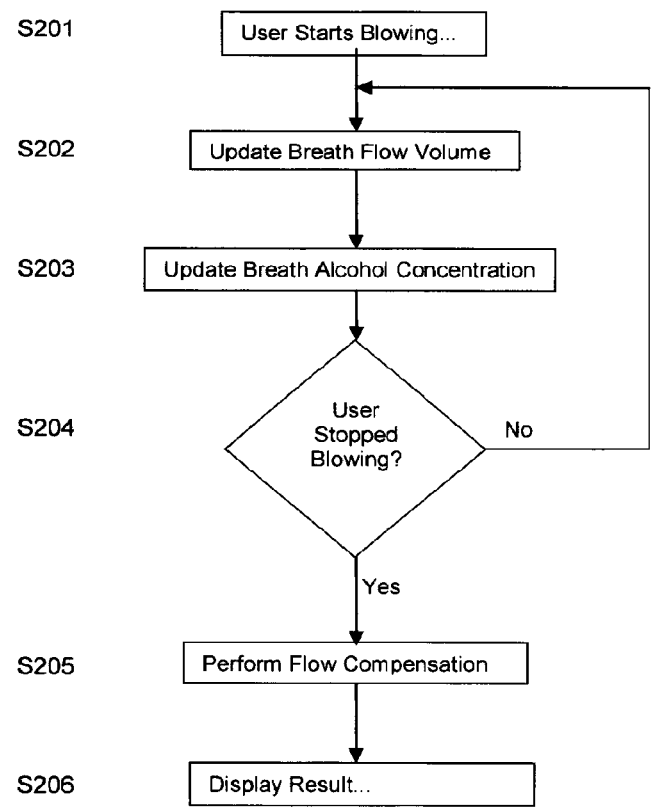
FIG. 2 is a flowchart illustrating the method according to the present invention.

FIG. 2 shows a flowchart illustrating the method according to the present invention. In a first step S201, the user starts blowing into a measuring apparatus, typically by means of a sampling tube or pipe made of plastic or other suitable material which is cheap to produce and replaceable, to ensure hygienic conditions to the users.

As the user continues to blow into the apparatus, the flow rate Q of the expired breath sample is measured and used to calculate the volume $V_b$ of the breath sample. In step S202 the calculated breath volume $V_b$ is continually updated throughout the measuring procedure by integrating the flow rate Q over time.

At the same time, the breath alcohol concentration BrAC is calculated from the fuel cell output signal $FC_{out}$ and is also continually updated in step S202 by integrating the fuel cell output signal $FC_{out}$ over time.

In step S204, it is checked whether the user has stopped blowing. If that is the case, flow compensation is performed in step S205 as explained above, whereby a final compensated value for the fuel cell output signal $FC_{comp}$ is obtained and used to calculate a compensated breath alcohol concentration $BrAC_{comp}$. This value may then be displayed to the user in step S206 and/or used to determine the blood alcohol concentration of the user.

Figure 3:
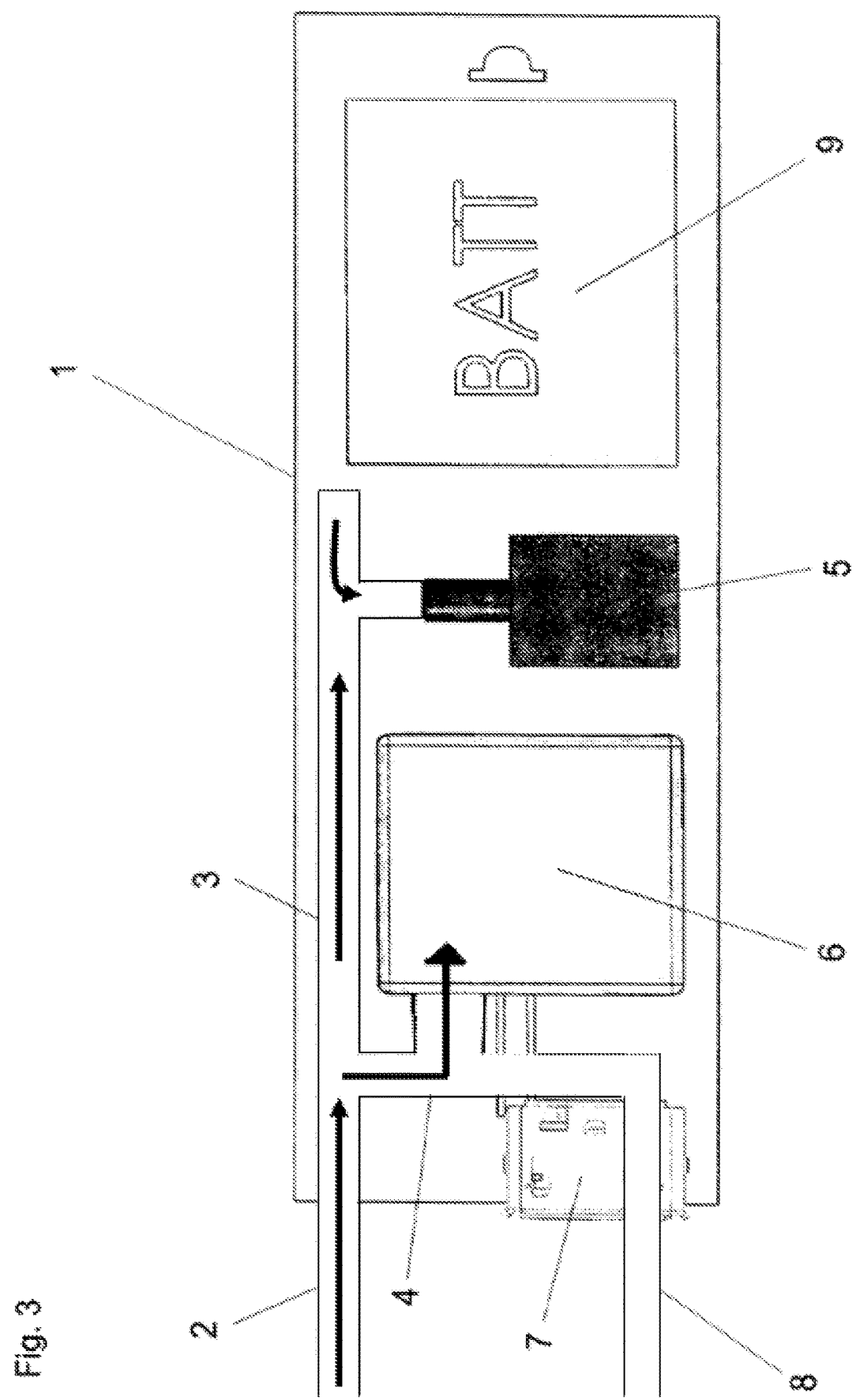
FIG. 3 is a schematic diagram of an apparatus according to the present invention.

FIG. 3 schematically shows an apparatus for measuring breath alcohol concentration BrAC, according to the present invention. The measuring apparatus is contained within a housing 1 and comprises a replaceable breath sample inlet tube 2 for receiving an expired breath sample from a user or test person. Arrows indicate the direction of breath flow through the measuring apparatus. The breath flow is led through a first channel 3 which is closed at a distal end. A flow meter 5 is located near the distal end of the first channel 3 and measures the instantaneous flow rate Q of the breath sample through the measuring apparatus 1.

In a preferred embodiment, flow meter 5 comprises a pressure-based flow meter such as a Venturi meter, an orifice plate or equivalent in combination with a pressure sensor. However the flow rate Q may be measured using any suitable flow meter, e.g. mechanical, pressure-based, optical, thermal or electromagnetic.

Part of the breath flow is led through a sampling channel 4 and enters a fuel cell sensor 6 near a proximal end of the first channel 3. Any alcohol (ethanol) present in the breath sample fuels an electrochemical reaction in the fuel cell 6 which gives rise to an electric current. This current then is a measure of the amount of alcohol in the breath sample and represented by a fuel cell output signal $FC_{out}$, normally the voltage measured across the fuel cell 6.

The flow meter 5 and the fuel cell 6 are connected with a microcontroller 7 which comprises means for processing the measurements of the flow rate and the fuel cell voltage. In this context, processing incorporates finding the area under the curves of the flow rate Q and the fuel cell output signal $FC_{out}$ versus time. The area corresponds to the volume $V_b$ of the breath sample and the breath alcohol concentration BrAC, respectively. This may also be achieved by integrating the flow rate Q, and the fuel cell output signal $FC_{out}$, respectively, with respect to time. The microcontroller 7 is adapted to continually update the breath sample volume $V_b$ and the fuel cell output signal $FC_{out}$ throughout the duration of the breath test.

When the breath sample has passed the fuel cell 6, it exits the housing 1 of the measuring apparatus through an exhaust tube 8.

Also comprised in the measuring apparatus is a battery 9 or other suitable source of energy to power the flow meter 5, the fuel cell 6 and/or the microcontroller 7.

In a preferred embodiment of the present invention, the measuring apparatus may further comprise display means to display the measured breath alcohol concentration BrAC and/or the blood alcohol concentration BAC. The blood alcohol concentration BAC may be determined from the blood-to-air partition ratio, i.e. the relation between the amount of alcohol in a given volume of breath and blood. Most breathalysers use an international standard partition ratio of 2100:1, that is, for every part alcohol in the breath there are 2100 parts alcohol in the blood.

The alcohol measuring apparatus according to the present invention may be made very compact and included in a sobriety interlock device. Such interlock devices are known in the art and will not be described in detail here. The interlock device may comprise means for measuring the temperature, humidity and/or alcohol concentration of the breath of a user, and based on these measurements falling within permitted ranges (corresponding to the user being non-intoxicated by alcohol), the interlock device allows starting up of a vehicle or other machinery connected to the interlock device. Further, the interlock device may be equipped with a microprocessor for analysing the results of the alcohol measuring apparatus and a relay electrically connected to the starter of the vehicle or machine.

When provided with an alcohol measuring apparatus according to the present invention, a compact and low-cost sobriety interlock device may be achieved and used to control start-up of any vehicle or machine.

What is claimed is:

1. A method of measuring a breath alcohol concentration (BrAC) of a user with a reduced lung capacity, the method measuring a flow rate (Q) of a breath sample, the breath sample having a breath sample volume $V_b$ that is variable, the method being performable without a sampling mechanism configured to measure a predetermined sample volume, the method comprising the steps of:

(I) receiving a flow of an expired breath sample from the user into an inlet tube, the inlet tube being adjacent to a proximal end of a first channel;

(II) receiving a first portion of the breath sample from the inlet tube into the first channel at the proximal end, wherein the first channel includes a closed distal end opposite the proximal end, and measuring an instantaneous flow rate (Q) of the first portion of the breath sample with a flow meter, the flow meter being disposed closer to the closed distal end of the first channel than to the proximal end;

(III) triggering a microcontroller in electronic communication with the flow meter to calculate the breath sample volume $V_b$ based on the measured instantaneous flow rate (Q);

(IV) receiving a second portion of the breath sample from the first channel into a second channel at a second channel entrance disposed closer to the proximal end of the first channel than to the distal end, and passing the second portion of the breath sample into a fuel cell sensor in electronic communication with the microcontroller and providing a fuel cell sensor output signal ($FC_{out}$);

(V) actuating the microcontroller to calculate the breath alcohol concentration (BrAC) based on the output signal ($FC_{out}$) of the fuel cell sensor;

(VI) updating continually the breath sample volume ($V_b$) and the breath alcohol concentration (BrAC) via the microcontroller by integrating the measured instantaneous flow rate (Q) and the fuel cell output signal ($FC_{out}$) over time, irrespective of the breath sample volume ($V_b$);

(VII) determining, via the microcontroller, an instant at which the flow of the expired breath sample from the user terminates, such that a final collected breath sample volume ($V_b$) is established; and (VIII) actuating the microcontroller to compensate the fuel cell sensor output signal ($FC_{out}$) using a stored calibration volume ($V_{cal}$) to obtain a final compensated fuel cell output signal ($FC_{comp}$), before calculating the breath alcohol concentration (BrAC) again when the user stops blowing; wherein said compensating is performed using a formula:

$$FC_{comp} = FC_{out} \frac{V_{cal}}{V_b},$$

such that the breath alcohol concentration (BrAC) is accurately calculated even when the breath sample volume ($V_b$) is varied.

2. The method according to claim 1, further comprising determining a blood alcohol concentration (BAC) based on the breath alcohol concentration (BrAC).

3. The method according to claim 2, further comprising displaying the resulting BAC on a display.

4. The method according to claim 2, wherein the BAC is determined relative to the BrAC based on a predetermined ratio.

5. The method according to claim 4, wherein the predetermined ratio is a ratio of 2100:1 of parts of alcohol in the breath to parts of alcohol in the blood.

6. The method according to claim 1, further comprising displaying the calculated BrAC on a display.

7. The method according to claim 1, further comprising preventing start-up of a vehicle if the calculated breath alcohol concentration (BrAC) exceeds a predetermined threshold value.

8. The method according to claim 1, wherein the breath sample volume $V_b$ is a predetermined value or is below the predetermined value.

9. The method according to claim 1, further comprising moving the second portion of the expired breath sample through an exhaust tube after passing the second portion of the breath sample through the fuel cell sensor.

10. An apparatus for measuring breath alcohol concentration (BrAC) of a user with a reduced lung capacity, the device configured to measure a flow rate (Q) of a breath sample, the breath sample having a breath sample volume $V_b$ that is variable, the apparatus being operable without a sampling mechanism configured to measure a predetermined sampling volume, the apparatus comprising:
(I) an inlet tube configured to receive an expired breath sample of a user;
(II) a first channel and a second channel, the first channel having a proximal end adjacent to the inlet tube and a closed distal end opposite the proximal end, the second channel having a second channel entrance disposed closer to the proximal end of the first channel than to the distal end of the first channel;
(III) a flow meter configured to measure an instantaneous flow rate (Q) of a first portion of the breath sample received in the first channel, the flow meter being disposed closer to the closed distal end than to the proximal end;
(IV) a fuel cell sensor in fluid communication with the second channel and configured to measure a second portion of the breath sample received in the second channel at the second channel entrance from the first channel; and
(V) a microcontroller in electronic communication with the flow meter and the fuel cell sensor, the microcontroller being configured to:
(a) calculate the breath alcohol concentration (BrAC) based on an output signal ($FC_{out}$) of the fuel cell sensor; and
(b) calculate the breath sample volume ($V_b$) based on the measured instantaneous flow rate (Q);
wherein the microcontroller is further adapted to:
(c) to continually update the breath sample volume ($V_b$) and the breath alcohol concentration (BrAC) by integrating the measured instantaneous flow rate (Q) and the fuel cell output signal ($FC_{out}$) over time, irrespective of the breath sample volume ($V_b$);
(d) determine an instant at which the expired breath sample terminates and calculate the breath sample volume ($V_b$) at this instant; and
(e) perform a flow compensation to obtain a final compensated fuel cell output signal ($FC_{comp}$) using a stored calibration volume ($V_{cal}$) wherein said flow compensation is performed using a formula:

$$FC_{comp} = FC_{out} \frac{V_{cal}}{V_b},$$

11. The apparatus according to claim 10, wherein the microcontroller is further adapted to determine a blood alcohol concentration (BAC) based on the breath alcohol concentration (BrAC).

12. The apparatus according to claim 11, wherein the BAC is determined relative to the BrAC based on a predetermined ratio of 2100:1 of parts of alcohol in the breath to parts of alcohol in the blood.

13. The apparatus according to claim 10, further comprising a battery configured to provide electrical power to the apparatus.

14. The apparatus according to claim 10, wherein the flow meter includes at least one of a Venturi meter or an orifice plate.

15. The apparatus according to claim 10, further comprising an exhaust tube configured to receive the breath sample from the fuel cell sensor.

16. The apparatus according to claim 10, further comprising a display to display the calculated BrAC.

17. The apparatus according to claim 10, wherein the breath sample volume $V_b$ is a predetermined value or is below the predetermined value.

18. A breath alcohol interlock device comprising an apparatus according to claim 10, the breath interlock device being configured to be used with a vehicle to prevent operation of the vehicle if the calculated breath alcohol concentration (BrAC) exceeds a predetermined threshold value.

* * * * *